US008652499B2

(12) United States Patent
Nakamura et al.

(10) Patent No.: US 8,652,499 B2
(45) Date of Patent: Feb. 18, 2014

(54) MEDICAL ANTIMICROBIAL COMPOSITION AND MEDICAL DEVICE COMPRISING THE SAME

(75) Inventors: Masataka Nakamura, Otsu (JP); Kazuhiko Fujisawa, Otsu (JP); Tsutomu Goshima, Otsu (JP)

(73) Assignee: Toray Industries, Inc., Tokyo (JP)

( * ) Notice: Subject to any disclaimer, the term of this patent is extended or adjusted under 35 U.S.C. 154(b) by 161 days.

(21) Appl. No.: 12/921,500

(22) PCT Filed: Mar. 5, 2009

(86) PCT No.: PCT/JP2009/054121
§ 371 (c)(1),
(2), (4) Date: Sep. 8, 2010

(87) PCT Pub. No.: WO2009/113438
PCT Pub. Date: Sep. 17, 2009

(65) Prior Publication Data
US 2011/0008403 A1 Jan. 13, 2011

(30) Foreign Application Priority Data
Mar. 10, 2008 (JP) ................. 2008-059108

(51) Int. Cl.
*A61M 31/00* (2006.01)
*A61K 31/80* (2006.01)
*A61L 15/44* (2006.01)

(52) U.S. Cl.
USPC ............ 424/411; 424/78.37; 424/48

(58) Field of Classification Search
USPC .................. 424/411, 78.37, 78.36
See application file for complete search history.

(56) References Cited

U.S. PATENT DOCUMENTS

| 2004/0249180 A1* | 12/2004 | Nakamura et al. ............ 556/443 |
| 2005/0048124 A1* | 3/2005 | Sarangapani ................. 424/486 |
| 2006/0067981 A1* | 3/2006 | Xia .............................. 424/428 |

FOREIGN PATENT DOCUMENTS

| JP | 54-17797 | 7/1979 |
| JP | 60-80457 | 5/1985 |
| JP | 06-009725 A | 1/1994 |
| JP | 10-081717 | 3/1998 |
| JP | 11-099200 | 4/1999 |
| JP | 2005-513173 A | 5/2005 |
| JP | 2005-518826 | 6/2005 |
| JP | 2006-509532 A | 3/2006 |
| JP | 2007-527448 A | 9/2007 |
| JP | 2008-083649 A | 4/2008 |
| WO | WO 2008/038719 A1 | 4/2008 |

OTHER PUBLICATIONS

International Search Report dated Mar. 31, 2009, application No. PCT/JP2009/054121.

* cited by examiner

*Primary Examiner* — Anoop Singh
*Assistant Examiner* — Anna Falkowitz
(74) *Attorney, Agent, or Firm* — RatnerPrestia

(57) ABSTRACT

A medical antimicrobial composition includes a siloxanyl structure-containing polymer and an ammonium group-containing polymer, which is excellent in transparency, flexibility and mechanical properties, and also excellent in adhesion to a base resin with good mechanical properties, particularly to a silicone resin. The medical antimicrobial composition includes an ammonium group-containing polymer compound dispersed in a siloxanyl structure-containing polymer and a medical device comprising the medical antimicrobial composition.

14 Claims, No Drawings

MEDICAL ANTIMICROBIAL COMPOSITION AND MEDICAL DEVICE COMPRISING THE SAME

CROSS-REFERENCE TO RELATED APPLICATIONS

This application is the U.S. National Phase application of PCT International Application No. PCT/JP09/054,121, filed Mar. 5, 2009, and claims priority of Japanese Patent Application No. 2008-059108, filed Mar. 10, 2008, the disclosures of both of which are incorporated herein by reference in their entirety for all purposes.

FIELD OF THE INVENTION

The present invention relates to a medical antimicrobial composition and a medical device comprising the same.

BACKGROUND OF THE INVENTION

In the medical field, the infectious disease caused while a medical device formed of a polymeric material such as polyurethane is kept inserted or self-retained in the body of a patient is considered a problem as one of complications. Hitherto, in order to prevent the infectious disease caused by an indwelling medical device, the medical device is immersed in an aqueous solution containing an antimicrobial agent or disinfectant such as chlorohexidine or povidone iodine for disinfection immediately before use. As another method, in the case where the medical device can be exchanged during treatment, it is frequently exchanged. However, it is evident that an antimicrobial agent or disinfectant vanishes from the surface of a catheter with the lapse of time and cannot sustain the effect of disinfection and that in the case where a medical device is used for a long period of time, the effect of disinfection gradually declines. Further, the frequent exchanges of medical devices impose large burdens on medical workers. Therefore, as means for further prevention of infection, medical devices are variously processed to be antimicrobial. Typical approaches include catheters covered on the surfaces with antimicrobial agents such as chlorohexidine and catheters covered on the surfaces with a layer containing a metal such as silver or copper or a compound thereof. These catheters employ a system in which a material with antimicrobial action is gradually released at a constant rate in the body of a patient, and show a good effect compared with the cases where catheters are disinfected immediately before they are used.

However, a system in which an antimicrobial material is gradually released is still limited in the period of use and cannot avoid that the potency gradually declines. With regard to metals such as silver and compounds thereof, the internal kinetics prevailing after they are gradually released is unknown and they may also be harmful to the human body. Further, in the case where silver remains in the medical device waste after use, any special action of recovering silver from the waste is necessary.

For these reasons, as an alternative to slowly releasable chemicals, various polymers having ammonium groups are proposed as antimicrobial polymers (Patent Document 1). However, these polymers cannot be easily processed and cannot be easily molded alone. Therefore, it is proposed that an article produced by molding a polymer with excellent mechanical properties is coated on the surface with any of such antimicrobial polymers, or that a mixture consisting of an antimicrobial polymer and a polymer with excellent mechanical properties is molded into an article (Patent Documents 2 and 3).

However, a base resin with good mechanical properties, particularly a silicone has a problem that it is poor in adhesion to another polymer, and it is difficult to coat the surface of a silicone with a polymer having ammonium groups. Further, there is another problem that if a polymer containing a siloxanyl structure such as a silicone resin is mixed with a polymer having ammonium groups, transparency is impaired. A material mainly composed of a silicone rubber and capable of gradually releasing an antimicrobial agent is also known, but it does not solve the problem of the aforementioned slow-releasing antimicrobial system (Patent Document 4).

Further, document 5 discloses a method comprising the steps of impregnating a polymer base with a solution of an alkoxysilane with a quaternary ammonium salt and polycondensing said alkoxysilane in such a manner as to form interpenetrating networks in said polymer base. However, such formation of alkoxysilane condensation product has a problem of raising the elastic modulus of the polymer base, for decreasing the flexibility thereof, and tending to lower the mechanical properties of the polymer base as the case may be.

[Patent Document 1] JP 54-17797 B
[Patent Document 2] JP 10-081717 A
[Patent Document 3] JP 11-99200 A
[Patent Document 4] JP 60-80457 A
[Patent Document 5] JP 2006-509532 A

SUMMARY OF THE INVENTION

The invention provides a medical antimicrobial composition in which an ammonium group-containing polymer compound is dispersed in a siloxanyl structure-containing polymer, which is excellent in transparency, flexibility and mechanical properties and also excellent in adhesion to a base resin with good mechanical properties, particularly to a silicone resin. Additionally, the invention provides a medical device comprising said medical antimicrobial composition.

Embodiments of the invention may have one or more of the following configurations.

[1] A medical antimicrobial composition characterized in that an ammonium group-containing polymer compound (A) is dispersed in a siloxanyl structure-containing polymer (B).
[2] A medical antimicrobial composition, according to [1] mentioned above, wherein if the number of hydroxyl groups bonded to the carbon atoms in the medical antimicrobial composition is OH and the number of ammonium nitrogens is N, then N/OH ratio is 0.001 to 0.5.
[3] A medical antimicrobial composition, according to [1] or [2] mentioned above, wherein 30% or more of the silicon atoms in the medical antimicrobial composition are silicon atoms derived from a polar siloxanyl monomer.
[4] A medical antimicrobial composition, according to any one of [1] through [3] mentioned above, wherein at least one component of the siloxanyl structure-containing polymer (B) has a structure obtained from the siloxanyl monomer represented by the following general formula (a)

$$M\text{-}L\text{-}Sx \qquad (a)$$

(where M denotes a radical polymerizable group; L denotes a substituted or non-substituted divalent organic group with 1 to 20 carbon atoms; and Sx denotes a siloxanyl group).
[5] A medical antimicrobial composition, according to any one of [1] through [4] mentioned above, wherein the L in the aforementioned formula (a) denotes either of the groups represented by the following general formulae (b) and (c):

$$—(CH_2)_j— \quad (b)$$

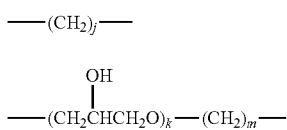
(c)

(where j denotes an integer of 1 to 20; k denotes an integer of 1 to 6; and m denotes an integer of 1 to 17; subject to 3k+m≤20).

[6] A medical antimicrobial composition, according to [5] mentioned above, wherein the L in the aforementioned formula (a) denotes a group represented by the general formula (c).

[7] A medical antimicrobial composition, according to any one of [4] through [6] mentioned above, wherein at least one component of the siloxanyl monomer is a polar siloxanyl monomer selected from the group consisting of the groups represented by the following formulae (e) and (g):

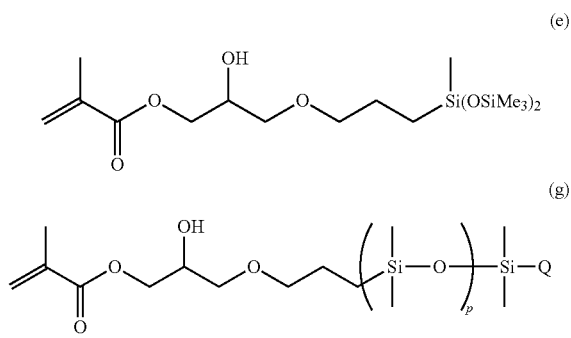

(in formula (g), Q denotes an alkyl group with 1 to 8 carbon atoms; and p denotes an integer of 1 to 20).

[8] A medical antimicrobial composition, according to any one of [1] through [7] mentioned above, wherein the ammonium group-containing polymer compound (A) has a structure obtained from the ammonium salt monomer represented by the following general formula (f):

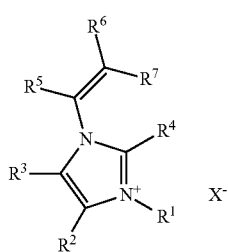

(where $R^1$ denotes a substituted or non-substituted alkyl group with 1 to 30 carbon atoms; $R^2$ to $R^7$ denote, respectively independently, a substituent group selected from hydrogen, substituted or non-substituted alkyl group with 1 to 20 carbon atoms, and substituted or non-substituted aryl group with 6 to 20 carbon atoms; $R^2$ and $R^3$ may also form a ring; and $X^-$ denotes a given anion).

[9] A medical antimicrobial composition, according to any one of [1] through [8] mentioned before, which is obtained by polymerizing the monomers and/or macromonomers constituting the siloxanyl structure-containing polymer (B) in a state of being mixed with the polymer compound (A).

[10] A medical device comprising the medical antimicrobial composition as set forth in any one of [1] through [9] mentioned above.

[11] A medical device, according to [10] mentioned above, which is at least partially covered with the medical antimicrobial composition as set forth in any one of [1] through [9] mentioned above.

[12] A medical device, according to [10] or [11] mentioned above, which is a molded article containing a silicone resin.

[13] A medical device, according to any one of [10] through [12] mentioned above, which has a form selected from a tube and a fine rod.

[14] A medical device, according to [13] mentioned before, which is one selected from an endoscope, catheter, infusion tube, gas transfer tube, stent, sheath, cuff, tube connector, access port, drain bag and blood circuit.

[15] A medical device, according to [13] mentioned above, which is a gastrostomy tube.

This invention can provide a medical antimicrobial composition in which an ammonium group-containing polymer compound is dispersed in a siloxanyl structure-containing polymer. Since said medical antimicrobial composition is excellent in transparency, flexibility and mechanical properties, the medical device comprising said composition can be enhanced in convenience and quality. Further, since said medical antimicrobial composition is excellent in adhesion to a base resin with good mechanical properties, particularly to a silicone resin, the base resin can be easily coated with said composition, and said medical antimicrobial composition is unlikely to peel during use.

DETAILED DESCRIPTION OF THE INVENTION

In an embodiment of the medical antimicrobial composition of this invention, an ammonium group-containing polymer compound (A) is dispersed in a siloxanyl structure-containing polymer (B). In this invention, siloxanyl means a structure containing at least one Si—O—Si bond. In an embodiment of this invention, said polymer compound (A) being dispersed in the siloxanyl structure-containing polymer (B) does not include the state where the polymer compound (A) is merely deposited on the surface of the siloxanyl structure-containing polymer (B), but refers to the state where after the medical antimicrobial composition has been ultrasonically washed on the surface using water, an attempt to extract the polymer compound contained in the medical antimicrobial composition using an organic solvent allows the ammonium group-containing polymer compound (A) to be extracted. In the case where the ammonium group-containing polymer compound (A) can be extracted by said extraction operation, it can be determined that said polymer compound (A) is dispersed in said siloxanyl structure-containing polymer (B). Particularly in the case where the ammonium group-containing polymer compound (A) can be extracted by 0.1% or more based on the dry weight of the medical antimicrobial composition by at least one of methanol, ethanol, 2-propanol, toluene, hexane, acetone, methyl ethyl ketone, ethyl acetate, butyl acetate, tetrahydrofuran and dimethyl sulfoxide used as organic solvents, it is determined that said polymer compound (A) is dispersed.

Methods for dispersing the polymer compound (A) into the siloxanyl structure-containing polymer (B) for obtaining the medical antimicrobial composition in an embodiment of this invention include a method comprising the step of producing the siloxanyl structure-containing polymer (B) by polymerization in the state where the polymer compound is mixed in a raw monomer mixture or raw macromonomer mixture of the siloxanyl structure-containing polymer (B), and a method comprising the step of immersing the siloxanyl structure-containing polymer (B) in the solution of the polymer compound (A) for impregnation, etc. The former method is preferred since the content of the polymer compound (A) can be enhanced.

In the case where the siloxanyl structure-containing polymer (B) is produced by polymerization in the state where the polymer compound (A) is mixed in the monomer mixture, if the content of the polymer compound (A) is too small, sufficient antimicrobial activity cannot be obtained, and if the content is too large, the solid content of the siloxanyl structure-containing polymer (B) becomes small. Therefore, it is preferred that the content of the polymer compound (A) is 0.1 to 20%. A more preferred range is 0.5 to 15%, and a further more preferred range is 1 to 10%. Each percentage is a percentage by weight expressed with the total weight (dry weight) of the polymer compound (A) and the siloxanyl structure-containing polymer (B) as 100.

In the case where the siloxanyl structure-containing polymer (B) is immersed in the solution of the polymer compound (A) for impregnation, any of various organic and inorganic solvents can be used for the solution of the polymer compound (A). Examples of the solvent include water, various alcohol solvents such as methanol, ethanol, propanol, 2-propanol, butanol, tert-butanol, tert-amyl alcohol and 3,7-dimethyl-3-octanol, various aromatic hydrocarbon solvents such as benzene, toluene and xylene, various aliphatic hydrocarbon solvents such as hexane, heptane, octane, decane, petroleum ether, kerosene, ligroin and paraffin, various ketone solvents such as acetone, methyl ethyl ketone and methyl isobutyl ketone, various ester solvents such as ethyl acetate, butyl acetate, methyl benzoate, dioctyl phthalate and ethylene glycol diacetate, and various glycol ether solvents such as diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, polyethylene glycol-polypropylene glycol block copolymer and polyethylene glycol-polypropylene glycol random copolymer. Any one of them can be used alone or two or more of them can also be used as a mixture. Among them, preferred are alcohol solvents, glycol ether solvents, water and mixtures consisting of two or more solvents selected therefrom. More preferred is water or a water-mixed solvent. Most preferred is water.

If the concentration of the solution of the polymer compound (A) is too low, sufficient antimicrobial activity cannot be obtained, and if the concentration is too high, it may be necessary to wash the excessive amount of the polymer compound. Therefore, it is preferred that the concentration is 0.1 to 30%. A more preferred range is 0.5 to 20%, and the most preferred range is 1 to 10%. Each percentage is a percentage by weight expressed with the total weight of the solution of the polymer compound (A) as 100.

As the hydrophilic monomer used in the siloxanyl structure-containing polymer (B) in an embodiment of the medical antimicrobial composition of this invention, a monomer having a (meth)acryloyl group, styryl group, allyl group, vinyl group or other polymerizable carbon-carbon unsaturated bond can be suitably used.

Preferred examples of the monomer include carboxylic acids such as (meth)acrylic acid, itaconic acid, crotonic acid and vinylbenzoic acid, (meth)acrylates having a hydroxyl group such as 2-hydroxyethyl (meth)acrylate, (meth)acrylamides such as N,N-dimethylacrylamide, N-vinylpyrrolidone, N-vinylimidazole, etc. Among them, in view the mechanical properties and long-term storage stability of the obtained siloxanyl structure-containing polymer (B), (meth)acrylamides such as N,N-dimethylacrylamide are preferred.

If the content of the siloxanyl component in the medical antimicrobial composition is too small, the medical antimicrobial composition used as a coating material is poor in adhesion to a silicone resin, etc., and if the content is too large, transparency is impaired. Therefore, it is preferred that the silicon atom content is 2 to 30 wt %, with the dry weight of the medical antimicrobial composition as 100 wt %. A more preferred range is 3 to 28 wt %, and the most preferred range is 5 to 25 wt %. The silicon atom content of the medical antimicrobial composition can be obtained by inductively coupled plasma atomic emission spectroscopy.

To obtain sufficient compatibility between the hydrophobic siloxanyl component of the siloxanyl structure-containing polymer (B) and the hydrophilic ammonium group-containing polymer compound (A), it is preferred that the silicon atoms derived from a polar siloxanyl monomer account for 30% or more of the silicon atoms in the siloxanyl component. More preferred is 40% or more, and most preferred is 50% or more.

In the above, the polar siloxanyl monomer refers to a siloxanyl monomer having a polar group in the molecule. Examples of the polar group include a hydroxyl group, amide group, carboxyl group, amino group, carbonate group, carbamate group, sulfoneamide group, sulfonic acid group, phosphonic acid group, alkoxy group with 1 to 3 carbon atoms, etc. In view of the effects of achieving the compatibility between the siloxanyl structure-containing polymer (B) and the polymer compound (A) and transparency, a hydroxyl group is most preferred.

Further, for enhancing transparency, it is preferred that the medical antimicrobial composition in an embodiment of this invention is copolymerized with a hydrophilic monomer, particularly a (meth)acrylate monomer having a hydroxyl group such as 2-hydroxyethyl (meth)acrylate. If the amount of the monomer used is too small, the effect of enhancing transparency is unlikely to be obtained, and if the amount is too large, the physical properties of the polymer are affected. Therefore, it is preferred that the amount of the monomer is 0.1 to 25 parts by weight per 100 parts by weight as the dry weight of the siloxanyl structure-containing polymer (B). A more preferred range is 0.5 to 20 parts by weight, and the most preferred range is 1.0 to 15 parts by weight.

Furthermore, if the N/OH ratio (where OH denotes the number of hydroxyl groups bonded to the carbon atoms in the medical antimicrobial composition, and N denotes the number of ammonium nitrogens) is too small, sufficient antimicrobial activity cannot be obtained, and if the ratio is too large, the obtained medical antimicrobial composition is not transparent enough. Therefore, it is preferred that the ratio is 0.001 to 0.5. A more preferred range is 0.005 to 0.4, and the most preferred range is 0.01 to 0.3. Moreover, the method for measuring the N/OH ratio is selected in response to the components of the siloxanyl structure-containing polymer (B) and the polymer compound (A) and the contents thereof. For example, general various measurement methods such as nuclear magnetic resonance (NMR), infrared spectroscopy (IR), elementary analysis, attenuated total reflection infrared absorption spectroscopy (ATR), ultraviolet spectroscopy (UV) and titration, and combinations thereof can be enumerated.

Polymerization methods for producing the siloxanyl structure-containing polymer (B) used in the medical antimicrobial composition in an embodiment of this invention include a method comprising the step of polymerizing a mixture consisting of various monomers such as a siloxanyl monomer, hydrophilic monomer and crosslinking monomer, a method comprising the steps of homopolymerizing or copolymerizing various monomers such as a siloxanyl monomer and hydrophilic monomer and subsequently polymerizing the macromonomers having polymerizable groups introduced therein, etc.

In the case where the siloxanyl structure-containing polymer (B) of the medical antimicrobial composition in an embodiment of this invention can be produced by polymerizing monomers, it is preferred that the siloxanyl monomer is a siloxanyl monomer with a structure having one polymerizable group in the molecule, represented by the following general formula (a):

$$M\text{-}L\text{-}Sx \qquad (a)$$

In the formula (a), M denotes a radical polymerizable group.
Examples of the radical polymerizable group include a vinyl group, allyl group, vinyloxy group, allyloxy group, vinyl carbamate group, allyl carbamate group, vinyl carbonate group, allyl carbonate group, methacryloyl group, acryloyl group, styryl group, etc. Among them, an acryloyl group and methacryloyl group are preferred in view of the elastic modulus of the obtained polymer.

In the formula (a), L denotes a substituted or non-substituted divalent organic group with 1 to 20 carbon atoms. In order to lower the elastic modulus of the obtained polymer, an alkylene group is more preferred, and in order to achieve the compatibility with the hydrophilic monomer, an organic group having a hydroxyl group or an ethylene oxide structure is more preferred. Examples of the organic group include divalent hydrocarbon groups such as methylene group, ethylene group, propylene group, methylethylene group, propylene group, butylene group, methylpropylene group, dimethylpropylene group and pentylene group, divalent organic groups having a hydroxyl group such as hydroxypropylene group and hydroxybutylene group, divalent organic groups having an ether bond represented by the following formulae (L-1) to (L-3), etc., divalent organic groups having an ether bond and a hydroxyl group together represented by the following formulae (L-4) and (L-5), etc.

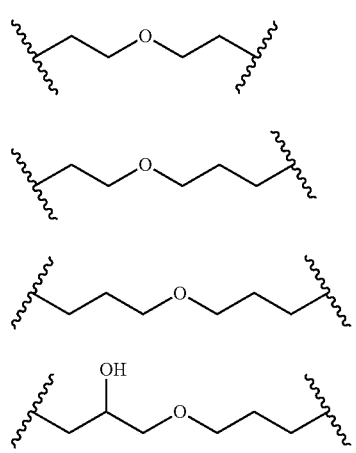

(L-1)
(L-2)
(L-3)
(L-4)
(L-5)

Among them, the group represented by the following formula (b) or (c)

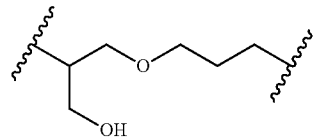

$$-(CH_2)_j- \qquad (b)$$

$$-(CH_2CHCH_2O)_k-(CH_2)_m- \qquad (c)$$
$$\qquad\quad\; |\;\;\;\;\;\;\;\;\;\;\;\;\;\;\;$$
$$\qquad\quad OH$$

is preferred, and the group represented by formula (c) is more preferred. Further, the group represented by formula (c) where k denotes 1 and m denotes 1 to 5 is preferred, and the group represented by formula (c) where k denotes 1 and m denotes 3 is most preferred.

In the formula (a), Sx denotes a siloxanyl group. In this case, the siloxanyl group refers to a group having at least one Si—O—Si bond in the structure thereof.

It is preferred that the siloxanyl monomer represented by the abovementioned general formula (a) is represented by the following general formula (a').

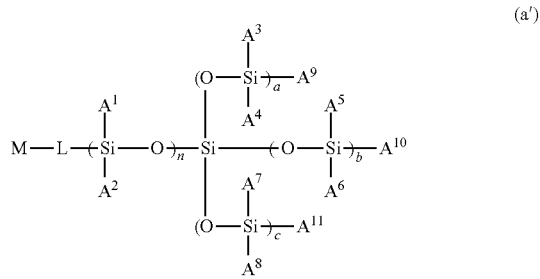

(a')

where n denotes an integer of 0 to 200; a, b and c denote, respectively independently, an integer of 0 to 20. The number of n+a+b+c decides the number of siloxane bonds in the siloxanyl compound. If the number of n+a+b+c is too small, the medical antimicrobial composition applied as a coating material is not sufficient in adhesion to a silicone resin, etc., and if the number is too large, the transparency is impaired. Therefore, it is preferred that the number is 1 to 260. A more preferred range is 2 to 100, and a further more preferred range is 2 to 50. The most preferred range is 2 to 15.

In the formula (a'), $A^1$ to $A^{11}$ denote, respectively independently, a substituted or non-substituted alkyl group with 1 to 20 carbon atoms or substituted or non-substituted aryl group with 6 to 20 carbon atoms. In the structure of the abovementioned formula (a'), among the substituent groups represented by the following formula (j)

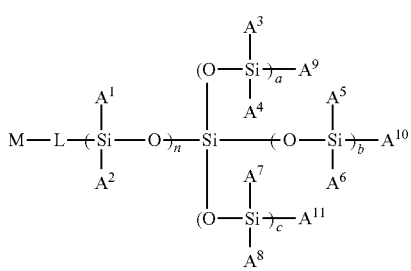

the especially suitable group can be selected from the group consisting of tris(trimethylsiloxy)silyl group, methyl-bis(trimethylsiloxy)silyl group, dimethyl(trimethylsiloxy)silyl group and poly(dimethylsiloxane) group for such reasons that a compound having such a substituent group is industrially available relatively at a low price and that a medical antimicrobial composition with high oxygen permeability and high transparency can be obtained. In this case, the poly(dimethylsiloxane) group is a substituent group represented by formula (j), where a=b=c=0; n denotes an integer of 2 to 15; each of $A^1$, $A^2$, $A^9$ and $A^{11}$ denotes a methyl group; and $A^{10}$ denotes an alkyl group with 1 to 10 carbon atoms, preferably a methyl group or butyl group, most preferably a butyl group.

Among the siloxanyl monomers represented by the general formula (a), the siloxanyl monomers represented by the following formulae (d), (e) and (g)

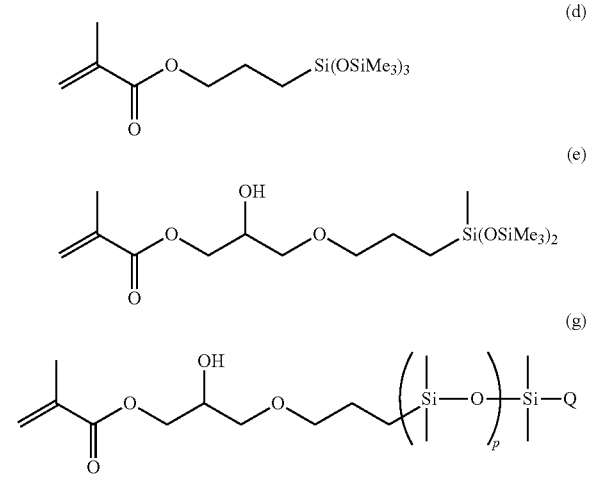

(in formula (g), Q denotes an alkyl group with 1 to 8 carbon atoms; and p denotes an integer of 1 to 20) are preferred in view of the compatibility with the hydrophilic monomer and ammonium salt monomer, and the oxygen permeability and mechanical properties of the polymer obtained by polymerization. Further, a siloxanyl monomer having a hydroxyl group in the molecule as represented by formula (e) or (g) is most preferred for the reason that even if the siloxanyl monomer is mixed with an internal wetting agent such as polyvinylpyrrolidone, a transparent siloxanyl structure-containing polymer can be easily obtained.

In this description, a macromonomer refers to a monomer with a molecular weight (formular weight) of 800 or more having one or more polymerizable groups. In the case where the siloxanyl structure-containing polymer (B) used in the medical antimicrobial composition in an embodiment of this invention is obtained from macromonomers, a method comprising the steps of homopolymerizing any of the abovementioned various siloxanyl monomers, subsequently introducing polymerizable groups then copolymerizing it with any of various hydrophilic monomers, etc., or a method comprising the steps of copolymerizing any of various siloxanyl monomers, any of various hydrophilic monomers, etc. and subsequently introducing polymerizable groups then polymerizing it can be used. Among these methods, a method of copolymerizing any of various siloxanyl monomers and any of various hydrophilic monomers and subsequently introducing polymerizable groups then polymerizing it is preferred since the compatibility between the siloxanyl component and the hydrophilic component tend to be high.

If the weight average molecular weight of the siloxanyl macromonomer is too low, the effect of inhibiting polymerization shrinkage as one of the advantages of using a macromonomer is insufficient, and if it is too high, such problems that the viscosity of the macromonomer becomes so high as to inconvenience handling and that the solubility in the polymerization solvent declines arise. Therefore, it is preferred that the weight average molecular weight is 1,000 to one million. A more preferred range is 3,000 to 500,000, and the most preferred range is 5,000 to 100,000. The weight average molecular weight is obtained by analyzing under the following conditions using size exclusion chromatography.

Columns: TSKgel Super HM-H two columns in series
Mobile phase: N-methylpyrrolidone (containing 10 mM of LiBr)
Column temperature: 40° C.
Flow rate of mobile phase: 0.2 mL/min
Measuring time: 40 minutes
Sample concentration: 0.4 wt % (N-methylpyrrolidone solvent)
Injected amount: 10 μL
In terms of standard polystyrene
Detector: RI detector The polymer compound (A) used in the medical antimicrobial composition in an embodiment of this invention is not a crosslinked polymer compound but a polymer compound that can be dissolved in a solvent.

The ammonium salt monomer constituting the polymer compound (A) used in the medical antimicrobial composition in an embodiment of this invention is a monomer having a polymerizable group and an ammonium group (ammonium cation) in the molecule. As the polymerizable group, a radical polymerizable group is preferred, and can be a (meth)acryloyl group, (meth)acrylamide group, styryl group, allyl group, vinyl group or other radical polymerizable group having a carbon-carbon unsaturated bond. Further, one of preferred modes of the ammonium group (ammonium cation) is an alkyl group with 1 to 20 carbon atoms having one substituent group connected with a polymerizable group, on the nitrogen atom of the ammonium group, in which the other three substituent groups may be respectively independently substituted, or a substituted or non-substituted aryl group with 6 to 20 carbon atoms. Suitable examples of the aforementioned substituent group connected with a polymerizable group include a (meth)acryloyloxyethyl group, (meth)acryloyloxypropyl group, (meth)acryloylaminoethyl group, (meth)acryloylaminopropyl group, (meth)acryloyloxyethyl aminocarbonyloxy ethyl group, (meth)acryloyloxyethyl aminocarbonyloxy propyl group, styryl group, styrylethyl group, styrylmethyl group, etc. Further, another preferred mode of an ammonium group is a case where the nitrogen atom of the ammonium group constitutes a nitrogen-containing hetero ring. Preferred examples of the nitrogen-containing hetero ring include an imidazole ring, imidazolidine ring, pyrazole ring, pyrazolidine ring, pyrrole ring, pyrrolidine ring, oxazole ring, oxazolidine ring, isoxazole ring, isoxasolidine ring, piperidine ring, pyridine ring, pyrazine ring, piperazine ring, pyrimidine ring, pyridazine ring, morpholine ring, quinoline ring, indoline ring, etc. Among them, an ammonium salt monomer having an imidazole ring is especially preferred in view of the transparency of the medical antimicrobial composition. More particular examples of the structure are the ammonium salt monomers represented by the following general formulae (f), (h) and (i):

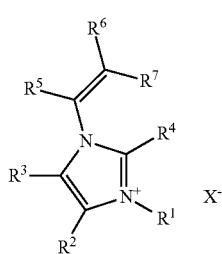

(f)

(in formula (f), $R^1$ denotes a substituted or non-substituted alkyl group with 1 to 30 carbon atoms; $R^2$ to $R^7$ denote, respectively independently, a substituent group selected from hydrogen, substituted or non-substituted alkyl group with 1 to 20 carbon atoms, and substituted or non-substituted aryl group with 6 to 20 carbon atoms; $R^2$ and $R^3$ may also form a ring; and $X^-$ denotes a given anion.)

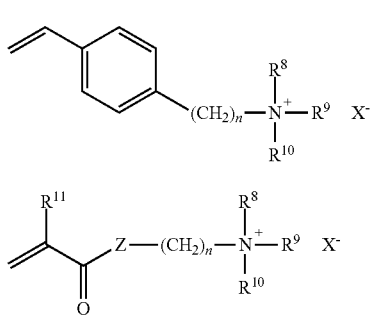

(h)

(i)

(in formulae (h) and (i), $R^8$ to $R^{10}$ denote, respectively independently, a substituted or non-substituted alkyl group with 1 to 20 carbon atoms or substituted or non-substituted aryl group with 6 to 20 carbon atoms; $R^{11}$ denotes hydrogen or methyl group; Z denotes O or NH; and $X^-$ denotes a given anion). Among them, a vinyl imidazolium salt represented by the general formula (f) is most preferred in view of the transparency, thermal stability and antimicrobial activity of the medical antimicrobial composition.

In the general formula (f), $R^1$ denotes a substituted or non-substituted alkyl group with 1 to 30 carbon atoms. If the number of carbon atoms is small, the compatibility with the siloxanyl monomer declines due to the hydrophilicity of the ammonium cation portion, and if the number of carbon atoms is too large, the compatibility with the hydrophilic monomer declines. Therefore, it is more preferred that the number of carbon atoms is 4 to 20. Suitable examples of the group are alkyl groups such as butyl group, hexyl group, octyl group, decyl group, undecyl group, dodecyl group, tetradecyl group, hexadecyl group and octadecyl group.

In the general formula (f), $R^2$ to $R^7$ denote, respectively independently, a substituted group selected from hydrogen, substituted or non-substituted alkyl groups with 1 to 20 carbon atoms and substituted and non-substituted aryl groups with 6 to 20 carbon atoms. Suitable examples of $R^2$ to $R^7$ include alkyl groups such as methyl group, ethyl group, propyl group, butyl group, hexyl group, octyl group, decyl group, undecyl group, dodecyl group, tetradecyl group, hexadecyl group and octadecyl group; substituted alkyl groups such as benzyl group; and aryl groups such as phenyl group. A more preferred example is hydrogen or methyl group, and the most preferred example is hydrogen. Further, in another mode, $R^2$ and $R^3$ may also form a ring. That is, $R^2$ and $R^3$ may be combined with each other to form a ring condensed to an imidazole ring. In this case, a suitable example of the condensed ring formed of $R^2$, $R^3$ and imidazole ring is a benzimidazole ring.

In the general formulae (h) and (i), $R^8$ to $R^{10}$ denote, respectively independently, a substituted or non-substituted alkyl group with 1 to 20 carbon atoms or substituted or non-substituted aryl group with 6 to 20 carbon atoms. Suitable examples of $R^8$ to $R^{10}$ include alkyl groups such as methyl group, ethyl group, propyl group, butyl group, hexyl group, octyl group, decyl group, undecyl group, dodecyl group, tetradecyl group, hexadecyl group and octadecyl group; substituted alkyl groups such as benzyl group; and aryl groups such as phenyl group.

In the general formulae (f), (h) and (i), $X^-$ denotes a given anion. Examples of the anion include halide ions such as fluoride ion, chloride ion, bromide ion and iodide ion, hydroxide ion, sulfate ion, nitrate ion and tetrafluoroboron ion, etc. Among them, in view of easy synthesis, a halide ion is preferred, and in view of solubility, a bromide ion or iodide ion is most preferred.

The polymer compound (A) in one aspect of this invention can be the homopolymer of an ammonium salt monomer or a copolymer with another monomer. If the total weight of the respective monomers in the copolymer is 100 parts by weight, it is preferred that the ammonium salt monomer content is 1 part by weight or more, since otherwise sufficient antimicrobial activity cannot be obtained. More preferred are 10 parts by weight or more, and most preferred are 30 parts by weight or more.

In the case where another monomer than the ammonium salt monomer is copolymerized to obtain the polymer compound (A) used in the medical antimicrobial composition in an embodiment of this invention, a monomer having a (meth) acryloyl group, styryl group, allyl group, vinyl group or other polymerizable carbon-carbon unsaturated bond can be used as the other monomer. Examples of the monomer include amide monomers such as N-vinylpyrrolidone, N,N-dimethylacrylamide, N-vinylformamide and N-vinylacetamide, monomers having a hydroxyl group such as 2-hydroxyethyl methacrylate, N-(2-hydroxyethyl)acrylamide and 2-(2-hydroxyethoxy)ethyl methacrylate, siloxanyl monomers such as 3-tris(trimethylsiloxy)silylpropyl methacrylate and polydimethylsiloxane with (meth)acryl group(s) at one end or both ends. Among them, amide monomers and monomers having a hydroxyl group are preferred since the compatibility with the ammonium salt monomer can be easily obtained. Among them, N-vinylpyrrolidone, N,N-dimethylacrylamide, 2-hydroxyethyl methacrylate and N-(2-hydroxyethyl)acrylamide are preferred. N-vinylpyrrolidone is most preferred.

If the weight average molecular weight of the polymer compound (A) used in the medical antimicrobial composition is too low, the polymer compound (A) is likely to be dissolved out from the medical antimicrobial composition, and if it is too high, the solubility of the polymer compound (A) in the monomer mixture and in the impregnation solution declines. Therefore, it is preferred that the weight average molecular weight is 1,000 to one million. A more preferred range is 5,000 to 500,000, and the most preferred range is 10,000 to 300,000.

If the content of the polymer compound (A) used in the medical antimicrobial composition is too small, sufficient antimicrobial activity cannot be obtained, and if it is too large, sufficient transparency cannot be obtained. Therefore, it is preferred that the content is 0.01 to 20 wt %. A more preferred range is 0.5 to 15 wt %, and the most preferred range is 1 to 10 wt %. Each percentage is a percentage by weight expressed with the dry weight of the medical antimicrobial composition as 100.

For the medical antimicrobial composition in an embodiment of this invention, a monomer having two or more copolymerizable carbon-carbon unsaturated bonds in each molecule can be used as a comonomer for such reasons that good mechanical properties can be obtained and that good resistance to disinfectants and cleaning fluids can be obtained. In this case, it is preferred that the copolymerization rate of the monomer having two or more copolymerizable carbon-carbon unsaturated bonds in each molecule is 0.1 to 20 wt % with the dry weight of the medical antimicrobial composition as 100 wt %. A more preferred range is 0.3 to 10 wt %, and a further more preferred range is 0.5 to 5 wt %.

The medical antimicrobial composition in an embodiment of this invention may contain an ultraviolet light absorber, coloring matter or colorant, etc. Further, the composition may also have an ultraviolet light absorber and dye or colorant, each having a polymerizable group, copolymerized therewith.

In the case where the medical antimicrobial composition in an embodiment of this invention is produced by polymerization, it is preferred to add a thermal polymerization initiator or photo polymerization initiator typified by a peroxide or azo compound. In the case where thermal polymerization is performed, an initiator with an optimum polymerization property at a desired reaction temperature should be selectively used. In general, an azo initiator or peroxide initiator with a 10-hour half-life temperature of 40° C. to 120° C. is suitable. Examples of the photo polymerization initiator include carbonyl compounds, peroxides, azo compounds, sulfur compounds, halogen compounds, metal salts, etc. Any one of these polymerization initiators can be used alone or two or more of them can also be used as a mixture. The amount of the initiator is about up to 1 wt %.

In the case where the medical antimicrobial composition in an embodiment of this invention is produced by polymerization, a polymerization solvent can be used. As the solvent, any of various organic and inorganic solvents can be used. Examples of the solvent include water, various alcohol solvents such as methanol, ethanol, propanol, 2-propanol, butanol, tert-butanol, tert-amyl alcohol and 3,7-dimethyl-3-octanol, various aromatic hydrocarbon solvents such as benzene, toluene and xylene, various aliphatic hydrocarbon solvents such as hexane, heptane, octane, decane, petroleum ether, kerosene, ligroin and paraffin, various ketone solvents such as acetone, methyl ethyl ketone and methyl isobutyl ketone, various ester solvents such as ethyl acetate, butyl acetate, methyl benzoate, dioctyl phthalate and ethylene glycol diacetate, and various glycol ether solvents such as diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, polyethylene glycol-polypropylene glycol block copolymer and polyethylene glycol-polypropylene glycol random copolymer. Any one of them can be used alone or two or more of them can also be used as a mixture.

The medical device in an embodiment of this invention comprises the aforementioned medical antimicrobial composition. One of preferred modes of the medical device in an embodiment of this invention is a molded article at least partially formed of the aforementioned medical antimicrobial composition. Another one of preferred modes of the medical device in an embodiment of this invention is a molded article at least partially formed of a base resin and at least partially covered with the aforementioned medical antimicrobial composition.

As the base resin, a resin generally used as medical devices is preferred. Examples of the resin include olefin resins such as polyethylene, polypropylene and cyclic polyolefin resins, vinyl resins such as polyvinyl chloride, polyvinyl acetate and polyvinyl alcohol, urethane resins, acrylic resins, epoxy resins, polyester resins, polyamide resins, phenoxy resins, natural rubbers, silicone resins typified by polydimethylsiloxane, and synthetic rubbers. Further, copolymers comprising the monomers constituting these polymers, mixtures of these polymers, and various copolymers and mixtures obtained by mixing a plasticizer, reinforcing agent, stabilizer, polymerization initiator, polymerization accelerator or contrast medium, etc. with these polymers can also be used. In the case of a copolymer, various copolymerization modes can be employed, and any of random copolymerization, block copolymerization and graft copolymerization can also be used. As the aforementioned base resin, a silicone resin is most preferred in view of chemical stability, heat resistance, etc.

The medical device in an embodiment of this invention can suitably at least partially have a form selected from a tube and a fine rod. Suitable examples of the medical device include an endoscope, catheter, infusion tube (including a gastrostomy tube), gas transfer tube, stent, sheath, cuff, tube connector, access port, drain bag and blood circuit.

In the case where the medical device in an embodiment of this invention is at least formed of a base resin and at least partially covered with the aforementioned medical antimicrobial composition, the polymerization methods and molding methods suitably used for obtaining the medical device formed of a base resin include injection molding, extrusion, cutting work, mold polymerization, etc. In this case, the medical device in an embodiment of this invention is at least partially covered with the aforementioned medical antimicrobial composition. Examples of the covering method in this case are described below.

A mixture consisting of the ammonium group-containing polymer compound (A) and the siloxanyl structure-containing polymer (B) is hereinafter referred to as CX.

A mixture consisting of the ammonium group-containing polymer compound (A) and the monomer composition destined to constitute the siloxanyl structure-containing polymer (B) by polymerization is hereinafter referred as CY.

Examples of the covering method include a method comprising the steps of immersing the molded article of the aforementioned base resin in a CX solution and subsequently taking it out of the solution, for drying, a method comprising the steps of spraying a CX solution to the aforementioned molded article and subsequently drying, a method comprising the steps of directly coating the aforementioned molded article with a CX solution using an absorbing body such as a brush, cloth or sponge impregnated with the CX solution and subsequently drying, a method comprising the steps of immersing the aforementioned molded article in the CY or a solution thereof, subsequently taking out, as required drying the solvent, and polymerizing, a method comprising the steps of spraying the CY or a solution thereof to the aforementioned molded article, subsequently as required drying the solvent, and polymerizing, a method comprising the steps of directly coating the aforementioned molded article with the CY or a solution thereof using an absorbing body such as a brush, cloth or sponge impregnated with the CY or the solution thereof, subsequently as required drying the solvent, and polymerizing, etc.

If the thickness of the applied medical antimicrobial composition is too thin, it is difficult to obtain sufficient antimicrobial activity, and if it is too thick, it tends to be difficult to insert the medical device into a fine body cavity. Therefore, it is preferred that the thickness is 0.1 µm to 5 mm. A more preferred range is 1 µm to 100 µm, and an especially preferred range is 5 µm to 50 µm.

Further, in the case where good adhesion is unlikely to be obtained when the molded article is covered with the medical antimicrobial composition, it is preferred that the molded article is treated to be reformed before it is coated with the medical antimicrobial composition. The reforming treatment method can be irradiation with electromagnetic waves (including light), irradiation with a corpuscular beam such as electron beam, plasma treatment, chemical vapor deposition treatment such as vacuum evaporation or sputtering, heating, base treatment, acid treatment, use of any other appropriate surface treating agent, and combinations thereof.

Among these reforming means, ultraviolet light irradiation, plasma treatment, base treatment and acid treatment are preferred since they are simple.

In ultraviolet light irradiation, a high pressure mercury lamp, low pressure mercury lamp or excimer light irradiation can be preferably used.

In plasma treatment, a chemically highly active layer can be formed, though the activity is either oxidative or reducing, depending on the gas used. Suitable examples of the gas used include inert gases such as nitrogen, carbon dioxide, argon, helium, neon and argon, fluorine-containing gases such as carbon tetrafluoride and chlorofluorocarbon, oxygen, hydrogen, air and mixed gases thereof.

As the device for applying the aforementioned plasma treatment, it is preferred to use a vacuum chamber equipped with a high-frequency, low-frequency or other transmitter, and a so-called atmospheric pressure plasma device can also be suitably used. In the atmospheric pressure plasma device, since a plasma gas state of atmospheric pressure can be formed, a surface layer can be activated simply without requiring a pressure reducing device or vessel. The treatment by a high frequency is very effective, and usually a device of 13.56 MHz can be preferably used. Further, the output can be appropriately selected in reference to the size of the device and the molded article to be treated, but is usually 10 to 500 W. The treatment time is selected likewise, but usually a period of about 10 to 20 minutes can provide a sufficient effect.

The base treatment or acid treatment can be performed, for example, by a method of bringing the molded article into contact with a basic or acidic solution or a method of bringing the molded article into contact with a basic or acidic gas, etc. More particular methods include, for example, a method of immersing the molded article into a basic or acidic solution, a method of spraying a basic or acidic solution or a basic or acidic gas to the molded article, a method of coating the molded article with a basic or acidic solution using a knife or brush, etc., a method of spin-coating or dip-coating the molded article with a basic or acidic solution, etc. The simplest method for obtaining a large reforming effect is to immerse the molded article into a basic or acidic solution.

Further, in the case where good adhesion is unlikely to be obtained when the molded article is covered with the medical antimicrobial composition, a method of coating the molded article with a primer beforehand can be preferably used. The primer used should be appropriately selected in response to the base resin used, but a solution with a bifunctional compound such as diphenylmethane diisocyanate, toluene diisocyanate or hexamethylene diisocyanate or a silane coupling compound such as RTV (room temperature vulcanizing) silicone dissolved in an organic solvent is a suitable example.

If the viscosity of a CX solution, CY or a solution thereof is too high, it is difficult to cover uniformly, and if it is too low, several covering operations may be necessary to obtain a covering layer with a suitable thickness, to lower working efficiency. Therefore, it is preferred that the viscosity of the solution with the mixture dissolved at a concentration of 3 to 20 wt %, preferably 5 to 10 wt % is 0.01 P to 100 P. A more preferred range is 0.05 P to 60 P, and an especially preferred range is 0.1 P to 40 P.

In the case where the medical device is at least partially formed of the medical antimicrobial composition, suitable polymerization methods and molding methods for producing the medical device of this invention include injection molding, extrusion, cutting work, mold polymerization, etc.

As an example, a case where the medical antimicrobial composition of this invention is molded by a mold polymerization method is explained below.

A mixture (CY) consisting of an ammonium group-containing polymer compound (A) and a monomer composition constituting a siloxanyl structure-containing polymer (B) is made to fill the cavity of a mold with a certain shape. Then, photo polymerization or thermal polymerization is performed to form the mixture in the shape of the mold. The mold is formed of a resin, glass, ceramic or metal, etc., but in the case of photo polymerization, an optically transparent material is used, and usually a resin or glass is used. When a molded article is produced, in most cases, a cavity is formed by two mold members facing each other, and is filled with the CY. However, depending on the shape of the mold and the properties of the CY, a gasket intended to let the molded article have a certain thickness and to prevent the leak of the filling CY may also be used together. In succession, the mold having the cavity filled with the CY is irradiated with active light such as ultraviolet light or heated in an oven or liquid tank, to polymerize the CY. A method of using both photo polymerization and heat polymerization by performing heat polymerization after photo polymerization or on the contrary performing photo polymerization after heat polymerization can also be employed. In the case of photo polymerization, irradiating the molded article with light containing much ultraviolet light for a short period of time (usually 1 hour or less), for example, with a mercury lamp or insect collection lamp as the light source is general. In the case of thermal polymerization, a condition of gradually heating from about room temperature to reach a temperature of 60° C. to 200° C., taking several hours to tens of hours is preferred for holding the optical uniformity and quality of the molded article and for enhancing the reproducibility.

The medical antimicrobial composition in an embodiment of this invention can be treated to be reformed by various methods. It is preferred to perform the reforming treatment of enhancing the water wettability of the surface.

Particular reforming methods include irradiation with electromagnetic waves (including light), irradiation with a corpuscular beam such as electron beam, plasma treatment, chemical vapor deposition treatment such as vacuum evaporation or sputtering, heating, base treatment, acid treatment, use of any other appropriate surface treating agent, and combinations thereof. Among these reforming means, base treatment and acid treatment are preferred since they are simple.

Examples of the base treatment or acid treatment include a method of bringing the medical antimicrobial composition into contact with a basic or acidic solution, a method of bringing the medical antimicrobial composition into contact with a basic or acidic gas, etc. More particular methods include, for example, a method of immersing the medical antimicrobial composition in a basic or acidic solution, a method of spraying a basic or acidic solution or a basic or acidic gas to the medical antimicrobial composition, a method of coating the medical antimicrobial composition with a basic or acid solution using a knife, brush, etc., a method of spin-coating or dip-coating the medical antimicrobial composition with a basic or acidic solution, etc. The simplest method for obtaining a large reforming effect is a method of immersing the medical antimicrobial composition in a basic or acidic solution.

The temperature at which the medical antimicrobial composition is immersed in a basic or acidic solution is not especially limited, but is usually in a range from about −50° C. to about 300° C. Considering working efficiency, a temperature range from −10° C. to 150° C. is more preferred, and the most preferred range is −5° C. to 60° C.

The optimum period of time during which the medical antimicrobial composition is immersed in a basic or acidic solution depends on the temperature, but generally a period of 0.1 to 100 hours is preferred. A period of 0.3 to 24 hours is more preferred, and a period of 0.5 to 12 hours is most preferred. If the contact period of time is too short, a sufficient treatment effect cannot be obtained, and if the contact period of time is too long, working efficiency and productivity decline while such adverse effects as lower oxygen permeability and lower mechanical properties may occur as the case may be.

Examples of the base include alkali metal hydroxides, alkaline earth metal hydroxides, various carbonates, various borates, various phosphates, ammonia, various ammonium salts, various amines, high molecular weight bases such as polyethyleneimine and polyvinylamine, etc. Among them, an alkali metal hydroxide is most preferred in view of low price and large treatment effect.

Examples of the acid include various inorganic acids such as sulfuric acid, phosphoric acid, hydrochloric acid and nitric acid, various organic acids such as acetic acid, formic acid, benzoic acid and phenol, various high molecular weight acids such as polyacrylic acid and polystyrenesulfonic acid. Among them, high molecular weight acids are preferred in view of high treatment effect and less adverse effects on other physical properties, and among them, polyacrylic acid is most preferred in view of acidity and solubility.

As the solvent of the basic or acidic solution, any of various inorganic and organic solvents can be used. Examples of the solvent include water, various alcohols such as methanol, ethanol, propanol, 2-propanol, butanol, ethylene glycol, diethylene glycol, triethylene glycol, tetraethylene glycol, polyethylene glycol and glycerol, various aromatic hydrocarbons such as benzene, toluene and xylene, various aliphatic hydrocarbons such as hexane, heptane, octane, decane, petroleum ether, kerosene, ligroin and paraffin, various ketones such as acetone, methyl ethyl ketone and methyl isobutyl ketone, various esters such as ethyl acetate, butyl acetate, methyl benzoate and dioctyl phthalate, various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether, various aprotic polar solvents such as dimethylformamide, dimethylacetamide, N-methyl-2-pyrrolidone, dimethylimidazolidinone, hexamethyl phosphoric triamide and dimethyl sulfoxide, halogen containing solvents such as methylene chloride, chloroform, dichloroethane, trichloroethane and trichloroethylene, and chlorofluorocarbon solvents, etc. Among them, water is most preferred in view of economy, simple handling, chemical stability, etc. As the solvent, a mixture consisting of two or more solvents can also be used. The basic or acidic solution used may also contain ingredients other than the basic or acidic substance and the solvent.

After completion of base treatment or acid treatment, the medical antimicrobial composition can be washed to remove the basic or acidic substance. As the washing solvent, any of various inorganic and organic solvents can be used. Examples of the solvent include water, various alcohols such as methanol, ethanol, propanol, 2-propanol, butanol, ethylene glycol, diethylene glycol, triethylene glycol, tetraethylene glycol, polyethylene glycol and glycerol, various aromatic hydrocarbons such as benzene, toluene and xylene, various aliphatic hydrocarbons such as hexane, heptane, octane, decane, petroleum ether, kerosene, ligroin and paraffin, various ketones such as acetone, methyl ethyl ketone and methyl isobutyl ketone, various esters such as ethyl acetate, butyl acetate, methyl benzoate and dioctyl phthalate, various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether, various aprotic polar solvents such as dimethylformamide, dimethylacetamide, N-methyl-2-pyrrolidone, dimethylimidazolidinone, hexamethyl phosphoric triamide and dimethyl sulfoxide, halogen containing solvents such as methylene chloride, chloroform, dichloroethane, trichloroethane and trichloroethylene, and chlorofluorocarbon solvents, etc.

As the washing solvent, a mixture consisting of two or more solvents can also be used. The washing solvent may also contain ingredients other than the solvent, for example, an inorganic salt, surfactant and cleaning agent.

The reforming treatment may also be applied to the medical antimicrobial composition as a whole or only to a portion such as the surface of the medical antimicrobial composition. If the reforming treatment is applied to the surface only, the water wettability of the surface only can be enhanced without greatly changing the nature of the medical antimicrobial composition as a whole.

Another method for enhancing the water wettability of the surface of the medical antimicrobial composition in an embodiment of this invention is an internal wetting agent method in which a monomer mixture to be polymerized is polymerized in the state where the monomer mixture contains a hydrophilic polymer to ensure that the medical antimicrobial composition may hold the hydrophilic polymer, to enhance the water wettability of the surface thereof. Examples of the hydrophilic polymer used as the internal wetting agent include polyvinyl cyclic amides such as polyvinylpyrrolidone, polyvinyl cyclic amines such as polyvinylimidazole, polyacrylamides such as poly-N,N-dimethylacrylamide, polyalcohols such as polyvinyl alcohol, polycarboxylic acids such as polyacrylic acid, polyethylene glycols, mixtures and copolymers thereof, etc. Among them, polyvinylpyrrolidone is most preferred in view of the water wettability enhancement of the surface of the medical antimicrobial composition.

It is not preferred that the oxygen permeability of the medical antimicrobial composition in an embodiment of this invention is too low for the reason that in the case where the medical antimicrobial composition is applied especially to an artificial lung or artificial heart-lung, etc., oxygen gas permeation is inhibited. It is not preferred either that the oxygen permeability is too high since the adhesion to a silicone resin declines. It is preferred that the oxygen permeability coefficient is $1\times10^{-11}$ to $800\times10^{-11}$ $(cm^2/sec)mLO_2/(mL \cdot hPa)$. More preferred is $10\times10^{-11}$ to $500\times10^{-11}$ $(cm^2/sec)mLO_2/(mL \cdot hPa)$.

With regard to the antimicrobial activity of the medical antimicrobial composition of this invention, in the case where the plate counts of three samples are measured using *Pseudomonas aeruginosa*, if the mean value of the three plate counts after completion of culture is within 4 times the mean value of the three initial plate counts before culture, it is determined that no proliferation occurred, and that the antimicrobial composition has an antimicrobial effect. It is more preferred that the mean value after completion of culture is 10% or less of the mean value of plate counts of controls and it is most preferred that the mean value after completion of culture is 1% or less of the mean value of plate counts of controls.

EXAMPLES

Embodiments of this invention are explained below particularly in reference to examples. Meanwhile, 2-propanol may be referred to as IPA as the case may be.

Working Example 1

Twenty eight point eight parts by weight of the siloxanyl compound represented by the following formula (y1)

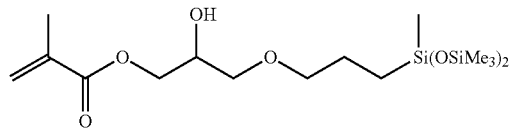

(y1)

35.5 parts by weight of N,N-dimethylacrylamide, 26.8 parts by weight of the polydimethylsiloxane methacrylated at one end represented by the following formula (y2)

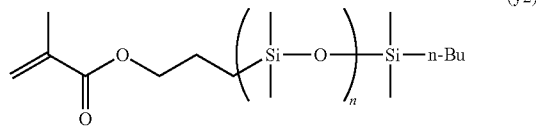

(y2)

("Silaplane" FM-0711 produced by Chisso Corporation, weight average molecular weight about 1,000), 3.8 parts by weight of 2-hydroxyethyl methacrylate, 3.0 parts by weight of tri(ethylene glycol) dimethacrylate, 5 parts by weight of an ammonium group-containing polymer compound (weight average molecular weight about 40,000, a copolymer of N-vinylpyrrolidone/vinylmethylimidazolium chloride 95/5.6 parts by weight), 1.0 part by weight of photo initiator Irgacure 1850, and 46 parts by weight of 3,7-dimethyl-3-octanol were mixed and stirred. The N/OH ratio of this composition was calculated and found to be 0.24. The monomer mixture was degassed in argon atmosphere. In a globe box in nitrogen atmosphere, two sheet of 100 μm thick "Parafilm" cut out in the central portions, were held as spacers between two 3 mm thick 10 cm square glass sheets (a gummed aluminum sheet was stuck to one of the glass sheets, to facilitate releasing), and the monomer mixture was poured into there and polymerized in the space between the sheets by light irradiation (Toshiba FL6D fluorescent lamp, 8.4 kiloluxes, 15 minutes), to obtain a sample film of a medical antimicrobial composition.

The sample films obtained as described above were exposed to ultrasonic waves in water for 20 minutes, released from the glass sheets, immersed in 60 wt % 2-propanol aqueous solution at 60° C. overnight, further immersed in 80 wt % 2-propanol aqueous solution at 60° C. for 2 hours, to extract impurities such as the remaining monomers, then being immersed in 50 wt % 2-propanol aqueous solution, 25 wt % 2-propanol aqueous solution and water lowered stepwise in IPA concentration one after another for 30 minutes each, to be hydrated. The sample films were immersed in a boric acid buffer (pH 7.1 to 7.3) in a 200 mL glass bottle, and the glass bottle was placed in an autoclave for boiling treatment at 121° C. for 30 minutes. The sample films were allowed to cool and subsequently taken out of the glass bottle, then being immersed in a boric acid buffer (pH 7.1 to 7.3). The obtained sample films were transparent and free from turbidity, being excellent in appearance quality. Further, when the sample films were touched by a finger for confirmation, they were found to be flexible, and when they were folded, they were not broken, being found to be excellent in mechanical properties. The obtained sample films were cut into 3 cm square sample films for evaluation of antimicrobial activity.

The sample film was dried in vacuum at 40° C. for 16 hours, and 2 g of it was taken, ultrasonically washed in distilled water for 30 minutes, then immersed in 2-propanol, and heated at 60° C. for 24 hours. From the extract, the solvent was distilled away using an evaporator, and a vacuum pump was used for reducing the pressure, to perfectly remove the remaining solvent. The extract was weighed and found to be 56.8 mg. Further, in reference to the infrared absorption spectrum, the extract was found to be N-vinylpyrrolidone/vinylmethylimidazolium chloride copolymer. From the result, it could be confirmed that the ammonium group-containing polymer compound had been dispersed in the aforementioned sample film.

Synthesis Example 1

Into a 50 mL eggplant type flask, 4.71 g (50 mmol) of N-vinylimidazole, 12.01 g (50 mmol) of n-octyl iodide and 0.1672 g of 2,6-di-t-butyl-4-methylphenol (BHT) were added and heated at 65° C. for 4 hours. After completion of reaction, the reaction product was purified using a column packed with 90 g of silica gel, using 360 mL of chloroform/methanol=50/1, 360 mL of chloroform/methanol=30/1, 360 mL of chloroform/methanol=20/1, 180 mL of chloroform/methanol=10/1 and 180 mL of chloroform/methanol=5/1 in this order as eluents. Thin layer chromatography was performed to collect fractions containing the intended spot, and an evaporator was used to distill away the solvent, for obtaining a yellow oily ammonium salt monomer represented by the following formula (x1).

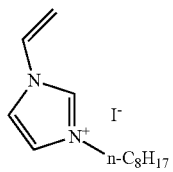
(x1)

Synthesis Example 2

One gram of the monomer represented by formula (x1) obtained in the abovementioned Synthesis Example 1, 1 g of 3,7-dimethyl-3-octanol and 0.02 g of photo initiator Irgacure 1850 were mixed and stirred. The monomer mixture was degassed in argon atmosphere, and poured into a laboratory dish with a diameter of 5 cm in a globe box in nitrogen atmosphere. It was irradiated with light (Toshiba FL6D fluorescent lamp, 8.4 kiloluxes, 15 minutes) and subsequently dissolved into an amount as small as possible of methanol, and the solution was added dropwise into 500 mL of ethyl acetate with stirring. The mixture was allowed to stand at 5° C. for 3 hours. It was filtered, to obtain a solid that was washed with a small amount of ethyl acetate. The pressure was reduced in a desiccator to distill away the solvent, for obtaining poly(vinyloctylimidazolium iodide) as the homopolymer of the monomer represented by the abovementioned formula (x1).

Working Example 2

Polymerization and post-processing were performed as described for Working Example 1, to obtain sample films for evaluation of antimicrobial activity, except that the monomer composition used was a mixture consisting of 22 parts by weight of the siloxanyl compound represented by formula (y1), 36 parts by weight of the siloxanyl compound represented by the following formula (y3)

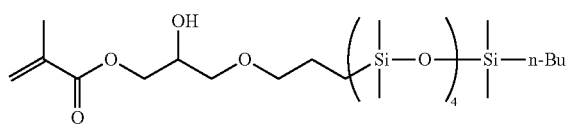
(y3)

28 parts by weight of N,N-dimethylacrylamide, 8 parts by weight of polyvinylpyrrolidone (K-90), 12 parts by weight of 2-hydroxyethyl methacrylate, 1 part by weight of tri(ethylene glycol) dimethacrylate, 1 part by weight of polydimethylsiloxane methacrylated at both the ends (X-22-164A produced by Shin-Etsu Chemical Co., Ltd.), 3.7 parts by weight of poly (vinyloctylimidazolium iodide) obtained in the abovementioned Synthesis Example 2, 1 part by weight of photo initiator Irgacure 1850 and 14 parts by weight of 3,7-dimethyl-3-octanol. The obtained sample films were transparent and free from turbidity, being excellent in appearance quality. Further, the sample films were touched by a finger for confirmation, and were found to be flexible. Further, when they were folded, they were not broken, being found to be excellent in mechanical properties.

Working Examples 3 and 4

Polymerization and post-processing were performed according to the method of Working Example 2, to obtain sample films for evaluation of antimicrobial activity, except that the amount of poly (vinyloctylimidazolium iodide) used was changed as shown in Table 1. The obtained sample films were transparent and free from turbidity, being excellent in appearance quality. Furthermore, the samples were touched by a finger for confirmation and found to be flexible. When they were folded, they were not broken, being found to be excellent in mechanical properties.

TABLE 1

|  | Amount of poly (vinyl-octylimidazolium iodide) used (parts by weight) | N/OH ratio |
|---|---|---|
| Working Example 2 | 3.7 | 0.05 |
| Working Example 3 | 5.0 | 0.07 |
| Working Example 4 | 10.0 | 0.14 |

Comparative Example 1

Sample films were obtained as described for Working Example 1, except that the polymer compound was not added to the monomer mixture. They were cut into 3 cm square sample films for evaluation of antimicrobial activity.

The sample obtained in Comparative Example 1 was dried in vacuum at 40° C. for 16 hours, and subsequently 2 g of it was taken and ultrasonically washed in distilled water for 30 minutes, then being immersed in 2-propanol and heated at 60° C. for 24 hours. An evaporator was used to distill away the solvent from the extract, and further a vacuum pump was used to reduce the pressure, for perfectly removing the remaining solvent. The extract was weighed and found to be 0.1 mg. Further, the solvent was changed to methanol, ethanol, toluene, hexane, acetone, methyl ethyl ketone, ethyl acetate, butyl acetate, tetrahydrofuran or dimethyl sulfoxide, to perform extraction, but in any of the cases, no extract in an amount corresponding to 0.1 wt % or more of the dry weight of the sample could be obtained.

Comparative Example 2

The sample films obtained in Comparative Example 1 were placed in a 50 mL screw tube, and immersed in 1.7% PVP/polymethylvinylimidazolium chloride (95/5) aqueous solution at room temperature for 16 hours.
Evaluation of Antimicrobial Activity Three sample films were prepared in each of Working Examples 1 to 4, and *Pseudomonas aeruginosa* NBRC 13275, one of typical bacteria observed in the use of contact lenses, was inoculated into the sample films according to 5.2 Test Method for Plastic Products, Etc. of JIS Z 2801:2000 "Antimicrobial Activity Test Methods and Antimicrobial Effects of Antimicrobially Processed Products." Immediately after the inoculation, the plate counts (initial plate counts) were determined, and after 24 hours at 35° C., the plate counts were determined for evaluation of antimicrobial activity. The results are shown in Tables 2 and 3. The sample films obtained in Comparative Example 1 in which polymerization was performed without the polymer compound showed proliferation compared with the initial counts. The sample films obtained in Working Example 1 showed plate counts smaller by one digit than the initial counts, and those obtained in Working Examples 2 to 4 showed plate counts smaller by five digits than the initial counts, showing sufficient antimicrobial activity.

TABLE 2

|  | Test 1 | Test 2 | Test 3 | Mean |
|---|---|---|---|---|
| Initial plate count | $2.72 \times 10^5$ | $2.64 \times 10^5$ | $2.33 \times 10^5$ | $2.6 \times 10^5$ |
| Working Example 1 | $4.62 \times 10^4$ | $4.23 \times 10^4$ | $3.45 \times 10^4$ | $4.1 \times 10^4$ |
| Comparative Example 1 | $6.26 \times 10^6$ | $6.90 \times 10^6$ | $6.41 \times 10^6$ | $6.5 \times 10^6$ |

TABLE 3

|  | Test 1 | Test 2 | Test 3 | Mean |
|---|---|---|---|---|
| Initial plate count | $3.15 \times 10^5$ | $3.45 \times 10^5$ | $3.60 \times 10^5$ | $3.4 \times 10^5$ |
| Working Example 2 | <10 | <10 | <10 | <10 |
| Working Example 4 | <10 | <10 | <10 | <10 |
| Working Example 4 | <10 | <10 | <10 | <10 |

Evaluation of Antimicrobial Activity After Ultrasonic Washing

The sample films obtained in Working Example 1 and Comparative Example 2 were immersed in 300 mL of distilled water and ultrasonically washed for 15 minutes, then being taken out for performing evaluation of antimicrobial activity as described above. The results are shown in Table 4. The sample films obtained in Comparative Example 2, which were immersed in an antimicrobial polymer aqueous solution only lost antimicrobial activity and showed the proliferation of the bacterium, but the sample films obtained in Working Example 1 showed sufficient antimicrobial activity still after ultrasonic washing.

The sample film obtained in Comparative Example 2 was dried in vacuum at 40° C. for 16 hours, and then 2 g of it was taken and ultrasonically washed in distilled water for 30 minutes, then being immersed in 2-propanol and heated at 60° C. for 24 hours. An evaporator was used to distill away the solvent from the extract, and further a vacuum pump was used to reduce the pressure, for perfectly removing the remaining solvent. The extract was weighed and found to be 0.3 mg. Further, the solvent was changed to methanol, ethanol, toluene, hexane, acetone, methyl ethyl ketone, ethyl acetate, butyl acetate, tetrahydrofuran or dimethyl sulfoxide, to perform extraction, but in any of the cases, no extract in an amount corresponding to 0.1 wt % or more of the dry weight of the sample could be obtained.

TABLE 4

|  | Test 1 | Test 2 | Test 3 | Mean |
|---|---|---|---|---|
| Initial plate count | $2.55 \times 10^5$ | $2.87 \times 10^5$ | $2.96 \times 10^5$ | $2.8 \times 10^5$ |
| Working Example 1 | $1.99 \times 10^3$ | $1.87 \times 10^3$ | $2.45 \times 10^3$ | $2.1 \times 10^3$ |
| Comparative Example 2 | $5.74 \times 10^6$ | $5.23 \times 10^6$ | $5.56 \times 10^6$ | $5.5 \times 10^6$ |

Working Examples 5 to 12

Polymerization and post-processing were performed as described for Working Example 1, to obtain sample films for evaluation of antimicrobial activity, except that the monomer composition was changed to a mixture consisting of $w_1$ parts by weight of the siloxanyl compound represented by formula (y1), $w_2$ parts by weight of the siloxanyl compound represented by formula (y3), $w_3$ parts by weight of the polydimethylsiloxane methacrylated at one end represented by formula (y2) ("Silaplane" FM-0711 produced by Chisso Corporation, weight average weight about 1,000), $w_4$ parts by weight methacryloxypropyltris(trimethylsiloxy)silane, $V_1$ parts by weight of N,N-dimethylacrylamide, 8 parts by weight of polyvinylpyrrolidone (K-90), $V_2$ parts by weight of 2-hydroxyethyl methacrylate, 1 part by weight of tri(ethylene glycol) dimethacrylate, 1 part by weight of polydimethylsiloxane methacrylated at both the ends (X-22-164A produced by Shin-Etsu Chemical Co., Ltd.), U parts by weight of the poly(vinyloctylimidazolium iodide) obtained in the above-mentioned Synthesis Example 2, 2 parts by weight of photo initiator Irgacure 1850 and 18 parts by weight of 3,7-dimethyl-3-octanol. The evaluation results of antimicrobial activity and the evaluation results of visual transparency of the obtained sample films are shown in Table 5. For comparison, the results of Working Example 2 are also shown in Table 5.

TABLE 5

|  | $w_1$ | $w_2$ | $w_3$ | $w_4$ | $V_1$ | $V_2$ | U | N/OH ratio | Antimicrobial activity | Transparency |
|---|---|---|---|---|---|---|---|---|---|---|
| Working Example 2 | 22 | 36 | 0 | 0 | 28 | 12 | 3.7 | 0.05 | Count smaller by 5 digits | Transparent |
| Working Example 5 | 22 | 36 | 0 | 0 | 28 | 12 | 10 | 0.15 | Count smaller by 5 digits | Transparent |
| Working Example 6 | 22 | 36 | 0 | 0 | 28 | 12 | 20 | 0.29 | Count smaller by 5 digits | Transparent |
| Working Example 7 | 22 | 36 | 0 | 0 | 28 | 12 | 30 | 0.44 | Count smaller by 5 digits | Moderately turbid |
| Working Example 8 | 22 | 36 | 0 | 0 | 28 | 12 | 40 | 0.59 | Count smaller by 5 digits | Highly turbid |
| Working Example 9 | 22 | 36 | 0 | 0 | 28 | 12 | 0.37 | 0.005 | Count smaller by 1 digit | Transparent |
| Working Example 10 | 22 | 36 | 0 | 0 | 28 | 12 | 0.8 | 0.012 | Count smaller by 3 digits | Transparent |
| Working Example 11 | 0 | 0 | 22 | 36 | 28 | 12 | 3.7 | 0.12 | Count smaller by 5 digits | Moderately turbid |
| Working Example 12 | 0 | 0 | 22 | 36 | 33 | 7 | 10 | 0.56 | Count smaller by 5 digits | Highly turbid |

$w_1$: Siloxanyl compound represented by formula (y1) (parts by weight)
$w_2$: Siloxanyl compound represented by formula (y3) (parts by weight)
$w_3$: Siloxanyl compound represented by formula (y2) (parts by weight)
$w_4$: Methacryloxypropyltris(trimethylsiloxy)silane (parts by weight)
$V_1$: N,N-dimethylacrylamide (parts by weight)
$V_2$: 2-hydroxyethyl methacrylate (parts by weight)
U: Poly(vinyloctylimidazolium iodide) (parts by weight)

Working Example 13

Polymerization and post-processing were performed according to the method of Working Example 2, to obtain sample films for evaluation of antimicrobial activity, except that the same amount of poly(N-methacryloxyethyl-N,N-dimethyl-N-butylammonium iodide) was used instead of poly(vinyloctylimidazolium iodide). The obtained sample films were somewhat turbid and inferior to the sample films obtained in Working Example 2 in view of transparency. The count as the evaluation result of antimicrobial activity was smaller by four digits.

Working Example 14

A monomer mixture consisting of 23 parts by weight of the siloxanyl compound represented by formula (y1), 35 parts by weight of the siloxanyl compound represented by formula (y3), 28 parts by weight of N,N-dimethylacrylamide, 8 parts by weight of polyvinylpyrrolidone (K-90), 12 parts by weight of 2-hydroxyethyl methacrylate, 1 part by weight of tri(ethylene glycol) dimethacrylate, 1 part by weight of polydimethylsiloxane methacrylated at both the ends (X-22-164A produced by Shin-Etsu Chemical Co., Ltd.), 3.7 parts by weight of poly(vinyloctylimidazolium iodide), 2 parts by weight of photo initiator Irgacure 1850 and 18 parts by weight of 3,7-dimethyl-3-octanol was degassed in argon atmosphere.

An urethra catheter made of a silicone resin was irradiated with an high frequency output of 40 W at an argon gas flow rate of 100 ml/min in a plasma reactor for 5 minutes. It was immediately immersed in the aforementioned monomer mixture in nitrogen atmosphere, and the monomer mixture was polymerized by light irradiation (Toshiba FL6D fluorescent lamp, 8.4 kiloluxes, 15 minutes), to obtain an urethra catheter covered with a medical antimicrobial composition.

The obtained urethra catheter was exposed to ultrasonic waves in water for 20 minutes and immersed in 60% IPA aqueous solution at 60° C. overnight, further immersed in 80% IPA aqueous solution at 60° C. for 2 hours, to extract impurities such as the remaining monomers, and immersed in 50% IPA aqueous solution, 25% IPA aqueous solution and water lowered stepwise in IPA concentration one after another for about 30 minutes each, to be hydrated. Finally, it was immersed in a boric acid buffer (pH 7.1 to 7.3).

Working Example 15

An infusion tube covered with a medical antimicrobial composition was obtained as described for Working Example 14, except that a tube (outer diameter 15 mm, inner diameter 12 mm, length 30 cm) made of a silicone resin was used instead of the urethra catheter made of a silicone resin.

Synthesis Example 3

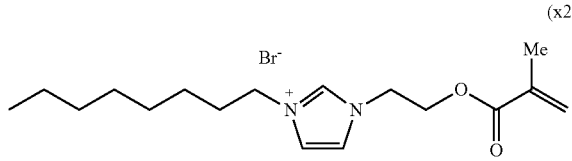

(x2)

One gram of the monomer represented by formula (x2), 1 g of 3,7-dimethyl-3-octanol and 0.02 g of photo initiator Irgacure 1850 were mixed and stirred. The monomer mixture was degassed in argon atmosphere, and poured into a laboratory dish with a diameter of 5 cm in a globe box in nitrogen atmosphere. It was irradiated with light (Toshiba FL6D fluorescent lamp, 8.4 kiloluxes, 15 minutes), and subsequently dissolved into an amount as small as possible of methanol, and the solution was added dropwise into 500 mL of ethyl acetate with stirring. Then the mixture was allowed to stand at 5° C. for 3 hours, and filtered, to obtain a solid that was washed with a small amount of ethyl acetate. The pressure was reduced in a desiccator to distill away the solvent, for obtaining the homopolymer of the monomer represented by the abovementioned formula (x2).

Working Example 16

Polymerization and post-processing were performed according to the method of Working Example 2, to obtain sample films, except that the homopolymer of the monomer represented by formula (x2) obtained in the aforementioned Synthesis Example 3 was used instead of poly(vinyloctylimidazolium iodide). The obtained sample films were transparent and free from turbidity, being excellent in appearance quality. Further, the sample films were touched by a finger for confirmation, and found to be flexible. When they were folded, they were not broken, being found to be excellent in mechanical properties.

Comparative Example 3

Twenty eight point eight parts by weight of the siloxanyl compound represented by formula (y1), 35.5 parts by weight of N,N-dimethylacrylamide, 26.8 parts by weight of the polydimethylsiloxane methacrylated at one end represented by formula (y2) ("Silaplane" FM-0711 produced by Chisso Corporation, weight average molecular weight about 1,000), 3.8 parts by weight of 2-hydroxyethyl methacrylate, 3.0 parts of tri(ethylene glycol) dimethacrylate, 10 parts by weight of the compound represented by the following formula (x3)

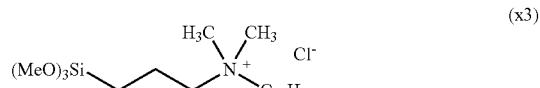

(x3)

1.0 part by weight of photo initiator Irgacure 1850 and 46 parts by weight of 3,7-dimethyl-3-octanol were mixed and stirred. The N/OH ratio of this composition was calculated and found to be 0.24. The monomer mixture was degassed in argon atmosphere. In a globe box in nitrogen atmosphere, two 100 μm thick Parafilms cut out in the central portions were held as spacers between two 3 mm thick 10 cm square glass sheets (an aluminum seal was stuck to one of the glass sheets, to facilitate releasing), and the monomer mixture was poured into there and polymerized in the space between the sheets by light irradiation (Toshiba FL6D fluorescent lamp, 8.4 kiloluxes, 15 minutes), to obtain a sample film of a medical antimicrobial composition.

The sample films obtained as described above were immersed in 0.1M sodium hydroxide aqueous solution (40° C.) for 3 hours, to proceed with polycondensation. Then, they were exposed to ultrasonic waves in water for 20 minutes, and peeled from the glass sheets, being immersed in 60 wt %

2-propanol aqueous solution at 60° C., and further immersed in 80 wt % 2-propanol aqueous solution at 60° C. for 2 hours, to extract impurities such as the remaining monomers, then being immersed in 50 wt % 2-propanol aqueous solution, 25 wt % 2-propanol aqueous solution and water lowered stepwise in IPA concentration one after another for about 30 minutes each, to be hydrated. The sample films were immersed in a boric acid buffer (pH 7.1 to 7.3) in a 200 mL glass bottle, and the glass bottle was placed in an autoclave, to perform boiling treatment at 121° C. for 30 minutes. After the sample films were allowed to cool, they were taken out of the glass bottle, and immersed in a boric acid buffer (pH 7.1 to 7.3). The obtained sample films were white turbid and were poor in appearance quality. Further, when the sample films were touched by a finger for confirmation, they were rather hard and poor in flexibility, and when they were folded, some were broken and found to be insufficient in mechanical properties.

The medical antimicrobial composition in an embodiment of this invention is suitable for medical uses as various drugs, medical adhesives, wound covering agents and medical devices, above all suitable for medical devices. Among medical devices, the medical antimicrobial composition is suitable for molded articles at least partially formed of a silicone resin. Further, the medical antimicrobial composition is especially suitable for medical devices at least partially having a form selected from a tube and a thin rod. Examples of the medical devices include an endoscope, catheter, infusion tube (including a gastrostomy tube), gas transfer tube, stent, sheath, cuff, tube connector, access port, drain bag and blood circuit.

The invention claimed is:

1. A medical antimicrobial composition comprising an ammonium group-containing polymer compound dispersed in a siloxanyl structure-containing polymer, wherein the ammonium group-containing polymer compound has a structure obtained from the ammonium salt monomer of general formula (f):

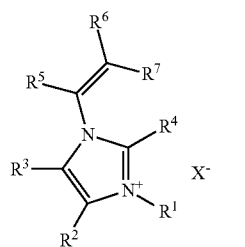

(f)

where $R^1$ is a substituted or non-substituted alkyl group with 1 to 30 carbon atoms; $R^2$ to $R^7$ are, respectively independently, a substituent group selected from hydrogen, substituted or non-substituted alkyl group with 1 to 20 carbon atoms, and substituted or non-substituted aryl group with 6 to 20 carbon atoms; $R^2$ and $R^3$ may also form a ring; and $X^-$ is a given anion, and wherein at least one component of the siloxanyl structure-containing polymer has a structure obtained from a siloxanyl monomer of general formula (a):

M-L-Sx    (a)

where M is a radical polymerizable group; L is a substituted or non-substituted divalent organic group with 1 to 20 carbon atoms; and Sx is a siloxanyl group.

2. A medical antimicrobial composition comprising an ammonium group-containing polymer compound dispersed in a siloxanyl structure-containing polymer, which is obtained by polymerizing monomers and/or macromonomers constituting the siloxanyl structure-containing polymer in a state of being mixed with the ammonium group-containing polymer compound, wherein the ammonium group-containing polymer compound has a structure obtained from the ammonium salt monomer of general formula (f):

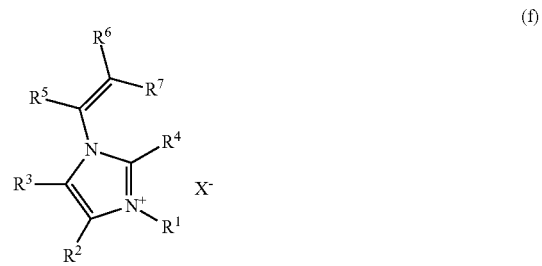

(f)

where $R^1$ is a substituted or non-substituted alkyl group with 1 to 30 carbon atoms; $R^2$ to $R^7$ are, respectively independently, a substituent group selected from hydrogen, substituted or non-substituted alkyl group with 1 to 20 carbon atoms, and substituted or non-substituted aryl group with 6 to 20 carbon atoms; $R^2$ and $R^3$ may also form a ring; and $X^-$ is a given anion, and wherein at least one component of the siloxanyl structure-containing polymer has a structure obtained from a siloxanyl monomer of general formula (a):

M-L-Sx    (a)

where M is a radical polymerizable group; L is a substituted or non-substituted divalent organic group with 1 to 20 carbon atoms; and Sx is a siloxanyl group.

3. The medical antimicrobial composition, according to claim 1 or 2, wherein if the number of hydroxyl groups bonded to the carbon atoms in the medical antimicrobial composition is OH and the number of ammonium nitrogens is N, then N/OH ratio is 0.001 to 0.5.

4. The medical antimicrobial composition, according to claim 1 or 2, wherein 30% or more of the silicon atoms in the medical antimicrobial composition are silicon atoms derived from a polar siloxanyl monomer.

5. The medical antimicrobial composition, according to claim 1 or 2, wherein the L is selected from the group consisting of formulae (b) and (c):

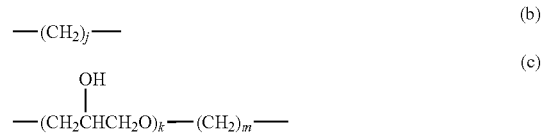

—(CH$_2$)$_j$—    (b)

—(CH$_2$CHCH$_2$O)$_k$—(CH$_2$)$_m$—    (c)
  |
  OH where j is an integer of 1 to 20; k is an integer of 1 to 6; and m is an integer of 1 to 17; subject to 3k+m≤20.

6. The medical antimicrobial composition, according to claim 5, wherein the L is formula (c).

7. The medical antimicrobial composition, according to claim 1 or 2, wherein at least one component of the siloxanyl monomer is a polar siloxanyl monomer selected from the group consisting of formulae (e) and (g):

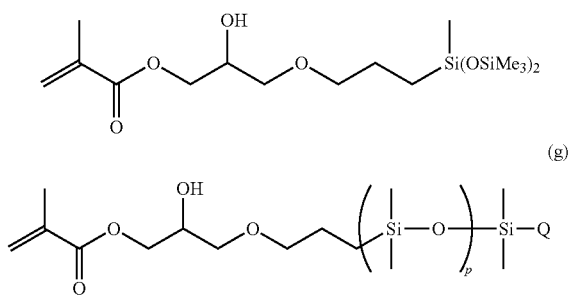

where in formula (g), Q is an alkyl group with 1 to 8 carbon atoms; and p is an integer of 1 to 20.

8. A medical device comprising the medical antimicrobial composition as set forth in claim 1 or 2.

9. A medical device at least partially covered with the medical antimicrobial composition as set forth in claim 1 or 2.

10. The medical device, according to claim 8, which is a molded article containing a silicone resin.

11. The medical device, according to claim 8, which has a form selected from a tube and a fine rod.

12. The medical device, according to claim 11, which is one selected from the group consisting of an endoscope, a catheter, an infusion tube, a gas transfer tube, a stent, a sheath, a cuff, a tube connector, an access port, a drain bag and a blood circuit.

13. The medical device, according to claim 11, which is a gastrostomy tube.

14. The medical antimicrobial composition according to claim 1 or 2, wherein the ammonium group-containing polymer compound (A) is present in a concentration of between 0.1 to 30%.

* * * * *